US00PP19430P3

(12) United States Plant Patent
Swartz

(10) Patent No.: US PP19,430 P3
(45) Date of Patent: Nov. 11, 2008

(54) RASPBERRY PLANT NAMED 'GEORGIA'

(50) Latin Name: ***Rubus ideaus* L.**
Varietal Denomination: Georgia

(75) Inventor: Harry J. Swartz, Laurel, MD (US)

(73) Assignee: University of Maryland, College Park, MD (US)

( * ) Notice: Subject to any disclaimer, the term of this patent is extended or adjusted under 35 U.S.C. 154(b) by 197 days.

(21) Appl. No.: 11/416,090

(22) Filed: May 2, 2006

(65) Prior Publication Data

US 2007/0261142 P1 Nov. 8, 2007

(51) Int. Cl.
*A01H 5/00* (2006.01)

(52) U.S. Cl. ..... Plt./204
(58) Field of Classification Search ..... Plt./204
See application file for complete search history.

(56) References Cited

U.S. PATENT DOCUMENTS

| | | | |
|---|---|---|---|
| PP10,411 | P | 5/1998 | Swartz et al. |
| PP10,412 | P | 5/1998 | Swartz et al. |
| PP10,610 | P | 9/1998 | Swartz et al. |
| PP11,313 | P | 3/2000 | Thomas |
| PP11,418 | P | 6/2000 | McNicol et al. |
| PP11,746 | P2 | 1/2001 | Sanford et al. |
| PP11,747 | P2 | 1/2001 | Sanford et al. |
| PP12,173 | P2 | 10/2001 | Swartz et al. |
| PP12,350 | P2 | 1/2002 | Swartz et al. |
| PP14,035 | P3 | 7/2003 | Hall |
| PP14,036 | P3 | 7/2003 | Hall |
| PP14,522 | P3 | 2/2004 | Moore |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP15,151 | P3 | 9/2004 | Ackerman |
| PP15,439 | P3 | 12/2004 | Ackerman |
| PP15,647 | P2 | 3/2005 | Swartz et al. |

*Primary Examiner*—Kent L. Bell
*Assistant Examiner*—Georgia Helmer
(74) *Attorney, Agent, or Firm*—Carter, Deluca, Farrell & Schmidt, LLP

(57) ABSTRACT

The present invention is a new and distinct floricane fruiting red raspberry cultivar named 'Georgia', which is capable of producing large quantities of fruit much earlier than that of the worldwide standard floricane cultivars, 'Glen Ample' and 'Tulameen'. The cultivar is characterized by its thornlessness and fruit with a slightly pileated drupelet. The fruit is also very symmetrical, light colored and round. Fruit aroma is very good and fruit firmness and sugar content is sufficient for shipping long distances.

10 Drawing Sheets

FIELD OF THE INVENTION

This invention concerns a new and distinct cultivar of floricane fruiting raspberry plant with a botanical name of *Rubus ideaus* L.

DESCRIPTION OF RELATED PRIOR ART

Several cultivars of spring bearing and fall bearing red raspberry plants are known. For instance, raspberry cultivars named 'Jaclyn', 'Anne', 'Caroline', 'Josephine', 'Kiwigold', PS-1703, PS-1764, Driscoll Cardinal, 'Driscoll Dolcita', 'Driscoll Maravilla', 'Driscoll Madonna', 'Driscoll Carmelina', 'Driscoll Francesca' and 'Motueka' have been described in U.S. Plant Pat. Nos. 15,647, 10,411, 10,412, 12,173, 11,313, 15,151, 15,439, 14,903, 14,904, 14,804, 14,781, 14,761, 14,860 and 14,035 respectively are all fall bearing or primocane fruiting types. Several cultivars of floricane fruiting (commonly known as "spring bearing") raspberry cultivars are known including 'Lauren', 'Tadmor' 'Glen Ample', 'Encore', 'Prelude', 'Emily' and WSU-1090 and have been described in U.S. Plant Pat. Nos. 10,610, 14,036, 11,418, 11,746, 11,747, 12,350, and 14,522 respectively.

The new and distinct cultivar of the present invention is a raspberry plant named 'Georgia'. This new and distinct cultivar of the present invention differs from 'Anne' and 'Kiwigold' in bearing red fruit, while 'Anne' and 'Kiwigold' bear yellow fruit. Compared with the recently patented fall bearing cultivars: 'Jaclyn', 'Caroline', 'Josephine', 'Kiwigold', PS-1703, PS-1764, 'Driscoll Cardinal', 'Driscoll Dolcita', 'Driscoll Maravilla', 'Driscoll Madonna', 'Driscoll Carmelina', 'Driscoll Francesca' and 'Motueka', 'Georgia' produces its crop in the spring. 'Georgia' can be distinguished from other spring bearing cultivars by several characteristics. 'Georgia' is thornless whereas 'Encore', 'Prelude', 'Emily', 'Lauren' and 'Tadmor' and WSU-1090 have thorns or bristles. Compared to 'Glen Ample', a thornless spring bearing cultivar, 'Georgia' is more winter hardy, much more vigorous in warm temperatures and its fruit has more compact, firmer and more cohesive drupelets, produced four days earlier on floricanes. 'Georgia' also has field resistance to root rot.

ORIGIN OF THE NEW CULTIVAR

The new cultivar of fall bearing red raspberry originated from a controlled cross at the University of Maryland Greenhouses in College Park, Md. The cross 'Glen Ample' (U.S. Plant Pat. No. 11,418)×PDW-4 (unpatented) was made in the winter of 1999 and designated "U" as a sequential breeding code designation for progenies. This year of crossing was designated: "T". Three hundred and fifty seeds were generated from this cross. From these seeds, 53 seedlings were planted in 2000. Only two seedlings survived the Phytophthora sp.-infested soil at this location. The clone was first selected in 2002 at Wye Research and Education Center, Queenstown, Md. and was therefore designated "–1". Thus, the complete breeding designation was "TU-1". The other surviving seedling, "TU-2" can be distinguished from TU-1 as it is thorny.

SUMMARY OF THE INVENTION

This application relates to a new and distinct red fruited, floricane fruiting, raspberry cultivar, botanically known as *Rubus ideaus* L. The following characteristics are outstanding:

1. Production of fruit on floricanes which is earlier than almost all other spring fruited commercially grown cultivars in the United Kingdom, an exception is, for example, 'Geln Moy', which is softer and grown for the pick-your-own trade.
2. In all the areas of test of this selection, 'Georgia' fruit is more cohesive than 'Glen Ample'. Fruit are as firm as all widely grown fresh market cultivars known to us, except being similar to 'Tulameen' (unpatened), 'Josephine' (U.S. Plant Pat. No. 12,173) and 'Summit' (unpatented).
3. Fruit size, cohesiveness, firmness and color are not severely reduced by temperatures between 80 and 90 F., this makes 'Georgia' adapted to tunnel culture that is necessary for rain and pest avoidance in the United Kingdom and California.
4. Compared to other early spring bearing cultivars such 'Glen Ample' and 'Lauren', a greater proportion of 'Georgia' floricanes have survived periodic late winter and spring frosts in diverse conditions as the United Kingdom and Maryland.
5. 'Gerogia' plants have field resistance to root rot incited by Phytophthora sp. Other cultivars with resistance to Phytophthora have smaller or less firm fruit or are thorny.

These characteristics make 'Georgia' suitable as a spring bearing floricane fruiting type for the United Kingdom and the Mid-Atlantic states. Its fruit size, relatively light fruit color, cohesiveness, ease of detachment and firmness make it ideal for commercial shipping. Its fruit flavor and size and plant thornlessness make it ideal for the pick-your-own market in the eastern US.

This cultivar was tested as an in-ground floricane bearer in Maryland and the United Kingdom, meaning overwintering canes were not removed. Typical varieties grown in Maryland, with the exception of 'Esta' (unpatented), experiences late winter and early spring cold temperature damage as a result of fluctuating warm and freezing temperatures.

The following characteristics are useful in distinguishing this cultivar from other cultivars and can be useful for cultivar identification.

1. The canes of 'Georgia' are thornless. Of 16 most recent cultivars given U.S. Plant Patents, only three, 'Glen Ample' (U.S. Plant Pat. No. 11,418), 'Tadmor' (U.S. Plant Pat. No. 14,036) and 'Motueka' (U.S. Plant Pat. No. 14,035) are claimed to be thornless. Primocanes, petioles and leaf veins are moderate green as most raspberries; however, the plant does not usually have any red coloration.
2. The mid-season fruit is round with a length to width ratio on midseason 3 gms fruit usually very close to 1:1. This ratio changes on larger and smaller fruit. 'Georgia' fruit also has a receptacle cavity a third of the diameter of its fruit. Thus, each of the two walls of the fruit and the cavity have the same thickness. These ratios are very similar to the typic round conic film and cohesive spring and fall bearing cultivar 'Josephine'.
3. 'Georgia' fruit is easy to pick, very firm, highly symmetrical, has an even collar and has a very slight amount of pubescence when ripe. 'Georgia' drupelets have a slight pileation where the dried style is attached, resulting in a distinctive downturning of the stigma-style. This pileation is also common for 'Glen Ample'. Compared to 'Glen Ample' (U.S. Plant Pat. No. 11,418). 'Georgia' has smaller drupelets. Fruit is very firm and cohesive when picked, color darkens only slightly to red-purple when overripe but the firmness and cohesiveness is retained in storage. Fruit rarely crumbles when picked, even when it is picked unripe.
4. The 5 green-grey sepals (Royal Horticultural Society colour plate No. 194A) often have a slight grey pink blush (Royal Horticultural Society colour plate No. 186C). This is very much less common in 'Glen Ample' and other cultivars.
5. Fruit are typically 4 days earlier to initiate ripening on floricanes than 'Glen Ample' (U.S. Plant Pat. No. 11,418), standard for spring production in the United Kingdom.

BRIEF DESCRIPTION OF THE PHOTOGRAPHS

The accompanying photographs show typical characteristics of the new variety:

DESCRIPTION OF THE NEW CULTIVAR

The following is a detailed description of the new cultivar, including fruit production, together with the cultivar's morphological characteristics. The characteristics of the cultivar were compared with other standards used in the Mid-Atlantic Region of the U.S. The description is based on information provided by cooperating scientists from plants grown in field, Kent, England, and from plants grown in the greenhouses at Collete Park, Md.

Figure 1:
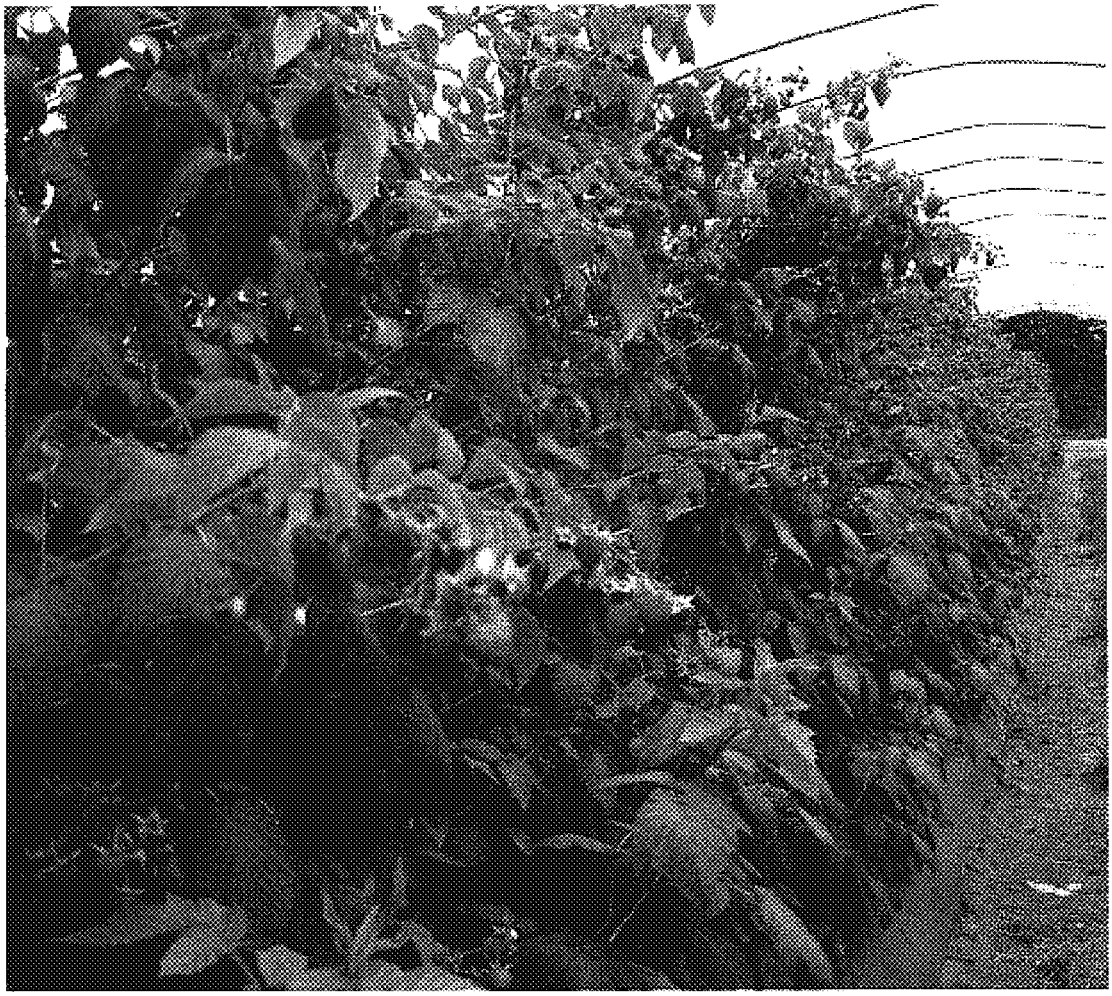
FIG. 1 shows a tunneled field of 'Georgia' at midseason fruiting. Plants are in their second growing season and exhibiting prolific suckering.
Figure 2:
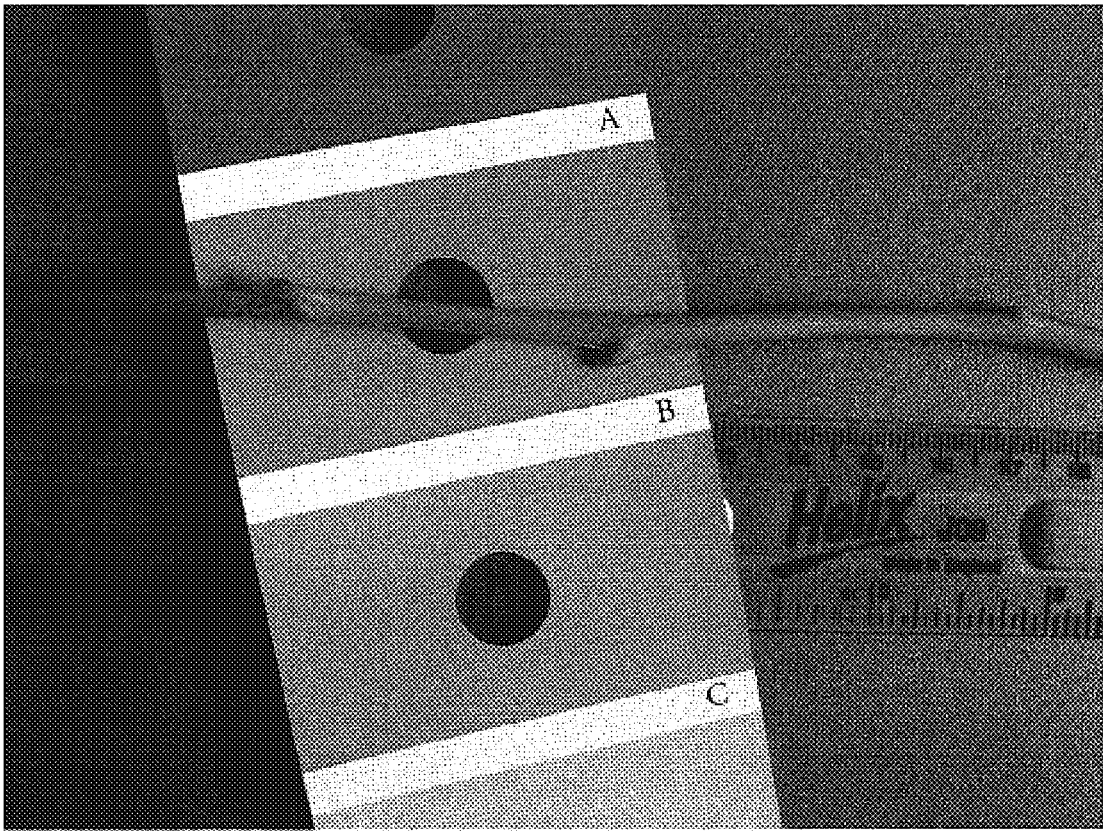
FIG. 2 shows a leafless, one-year old 'Georgia' primocane showing its thornlessness and color and Royal Horticultural Society colour plate No. 144.
Figure 3:
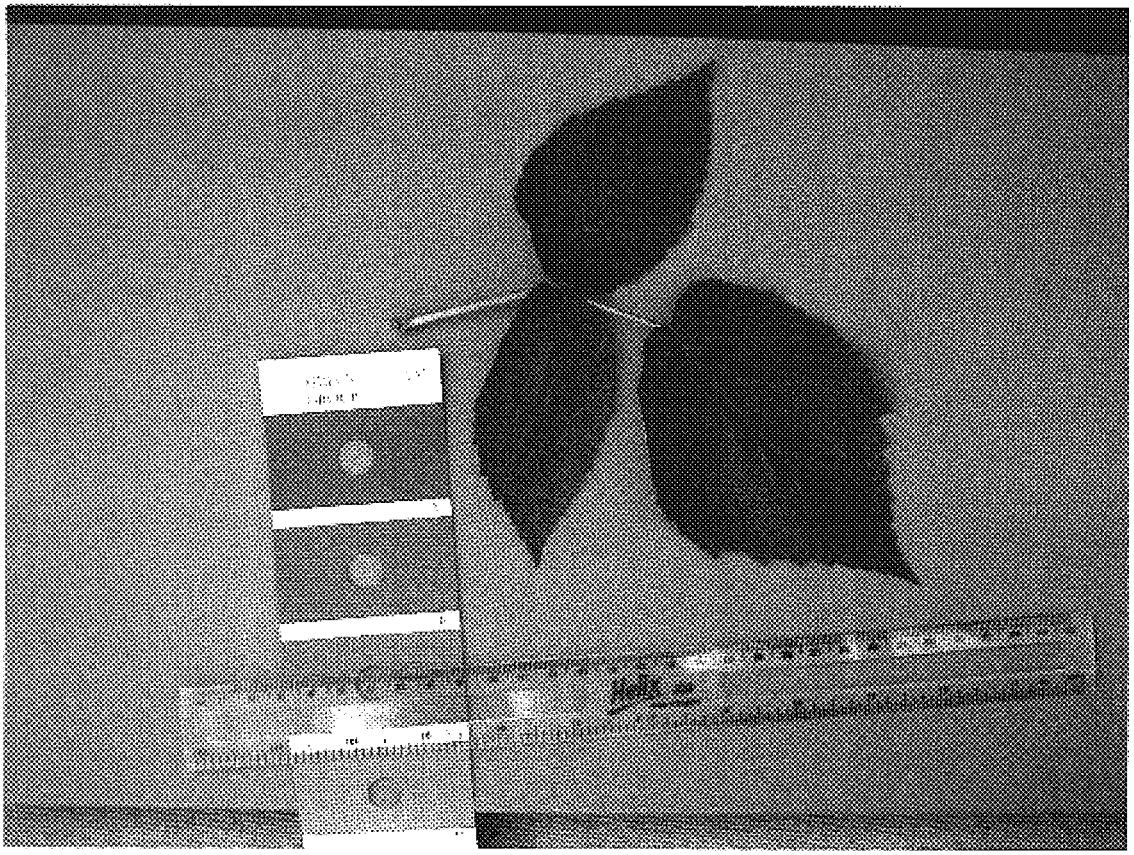
FIG. 3 shows the upper side of a one-year old 'Georgia' leaf, and a Royal Horticultural Society colour plate No. 137.

'Georgia' produces a very large number of root- and crown-suckers (FIG. 1), more than 'Anne' and 'Josephine', but similar to 'Caroline', 'Glen Ample' and 'Heritage'. In a controlled test in Kent, one year old 'Georgia' plants averaged 33 root suckers per pot compared to 29 per pot for 'Glen Ample'. During the growing season, canes are thornless, without red blush and light green colored (Royal Horticultural Society colour plate No. 144B (FIG. 2)). Canes are usually unbranched and erect to slightly arching by the second year of a plant's growth. On the second year canes, internode length averages 8.2 cm at the base and 14.7 cm at midcane. Growth is moderately vigorous, reaching on average 6 feet in full sun, or 8 feet in crowded conditions or in tunnels. Thorns are completely lacking. The upper surfaces of leaves are dark green, most closely in hue to Royal Horticultural Society colour Plate 137A (FIG. 3), depending on the amount of nitrogen fertilization and time of season.

Figure 4:
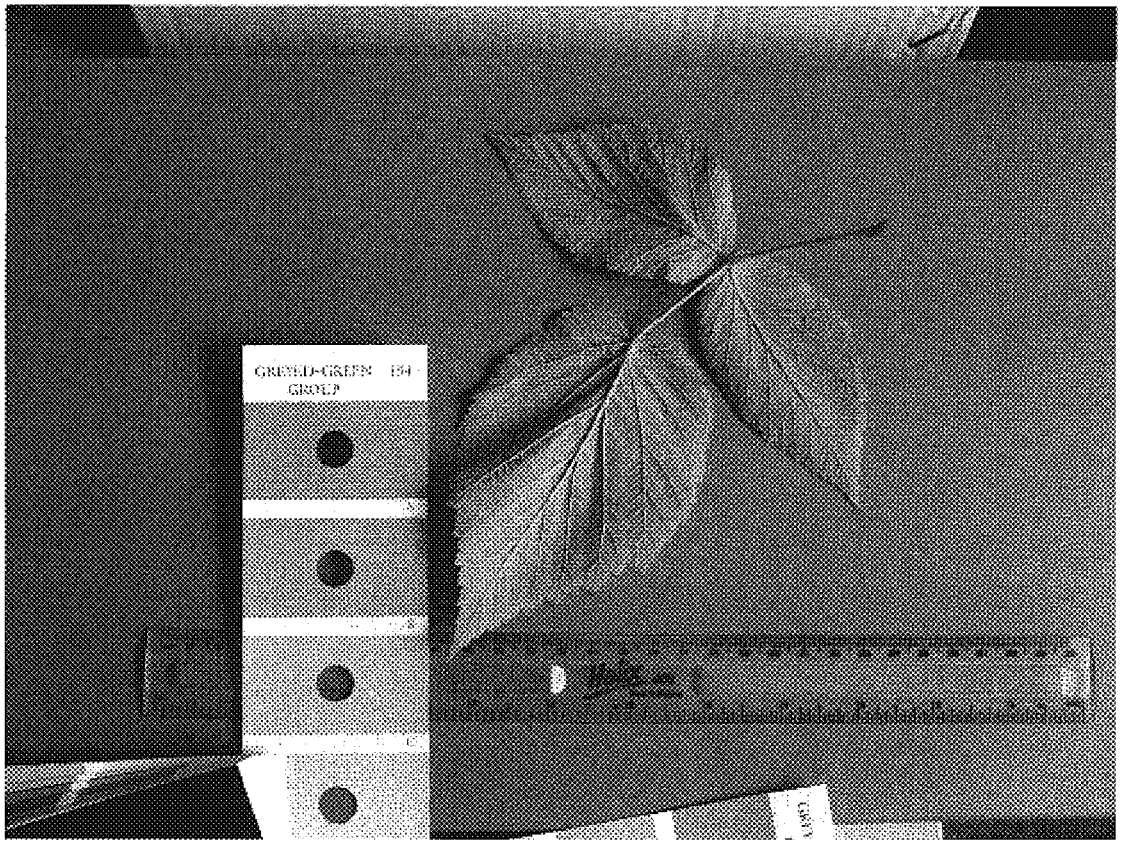
FIG. 4 shows the underside of a one-year old 'Georgia' leaf, and a Royal Horticultural Society colour plate No. 194.

Senescing leaves have a green yellow color resembling Royal Horticultural Society Colour Plate No. 146A. The lower surface of 'Georgia' leaves is pubescent grey-green resembling Royal Horticultural Society colour plate No. 194A (FIG. 4). Leaves are compound, that is, trifoliolate and pentafoliolate. Vigorous plants tend to have more pentafoliolate leaves. Trifoliolate and pentafoliolate terminal leaflet blade averages 11.2 cm and 11.4 cm in length respectively. Trifoliolate and pentafoliolate terminal leaflet blade averages 9.9 cm and 7.7 cm in width respectively. The trifoliolate leaves are wider because they have lobes from the formation of non-detached leaflets. The basal leaflets of trifoliolate and pentafoliolate leaves average 18.3 cm and 22.5 cm from terminal point to point respectively. The petiolules (the leaf stalk of the leaflets only) of trifoliolate leaves average 3.4 cm, compared to the pentafoliolate leaves 4.3 cm length basal and 2.4 cm length apical petiolules, for a total length of 6.7 cm. Trifoliolate and pentafoliolate petioles on primocanes average 6.0 and 6.2 cm respectively. The ratio the petiole length to petiolule is 1.75 to 1 for trifoliolate leaves and 1 to 1.1 for combined petiolules on pentafoliolate leaves. Lateral leaflets are sessile. Leaf serration, laminar puckering and veination pattern are common for most cultivars of red raspberry and cannot be used to distinguish this cultivar.

Figure 5:
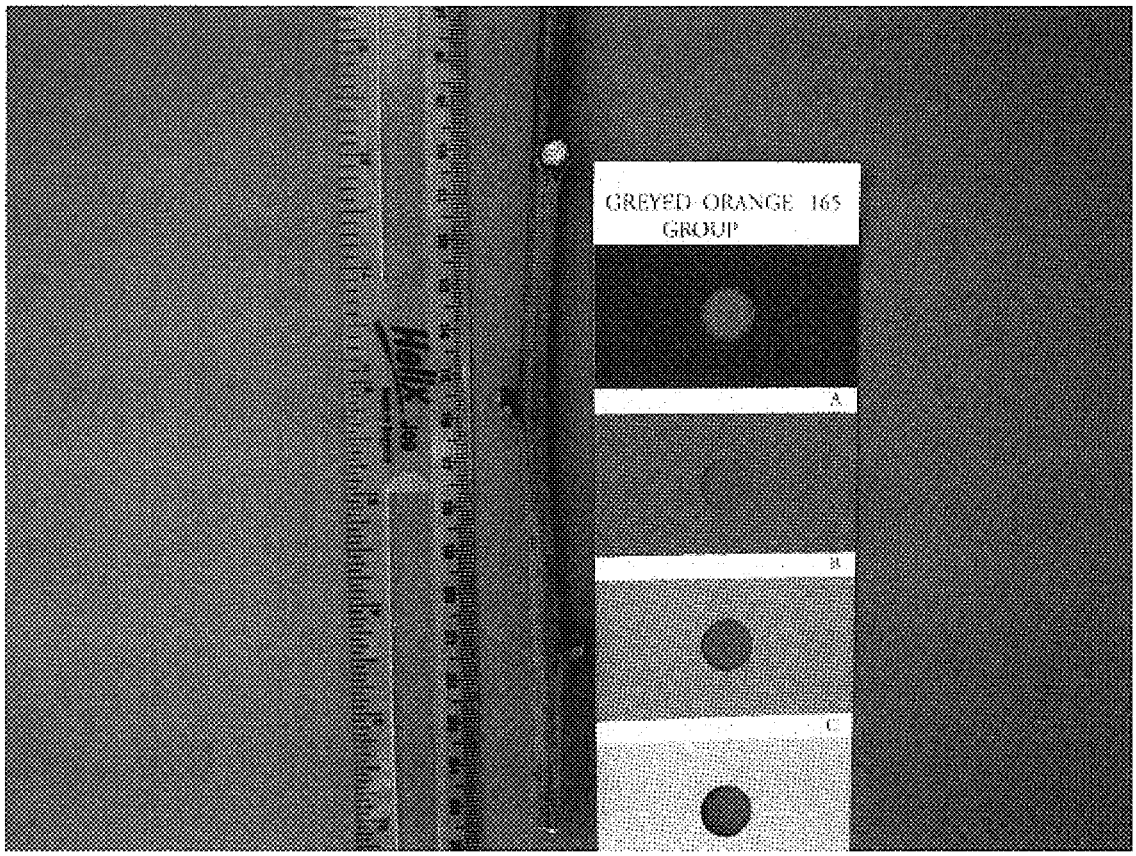
FIG. 5 shows the midsection of a mature floricane in mid-November (entering its $2^{nd}$ year) with Royal Horticultural Society colour plate No. 165.

Leaves abscise readily in October and November and coloration changes and exfoliation indicative of the change to a floricane occurs in October and November. 'Georgia' floricanes are orange-brown in color, resembling in hue Royal Horticultural Society colour plate No. 165, but varying in color intensity from A to C in a random pattern (FIG. 5). The bases of floricanes exfoliate to a moderate amount when the canes are greater than 1.5 cm in diameter. 'Georgia' canes are winter hardy in areas where temperatures do not drop below −20° C. No tests have been made in colder areas. Canes require less than 1000 chilling hours, however, canes have good bud break and growth even after fluctuating warm and freezing temperatures in March and April.

Figure 6:
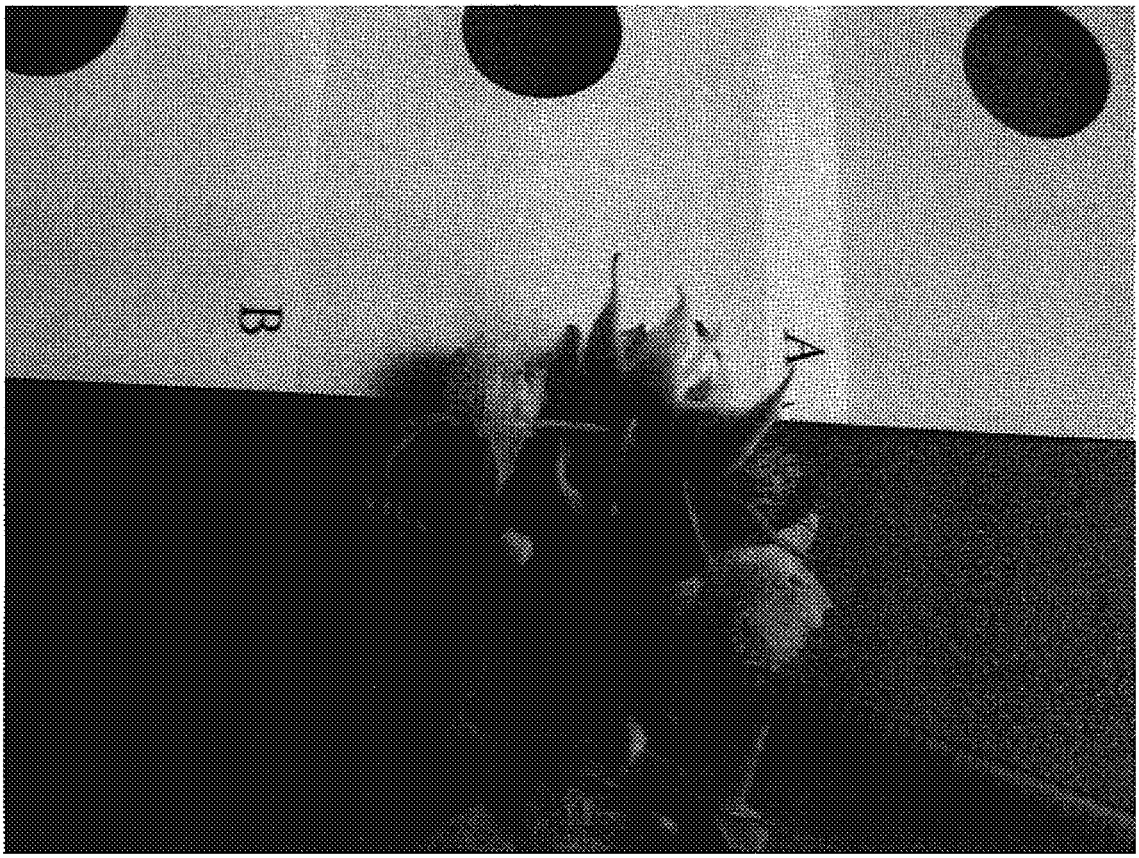
FIG. 6 shows the development of 'Georgia' flowers and immature fruit and Royal Horticultural Society colour plate 158 (depends on pix) ($2^{nd}$ growing season).
Figure 7:
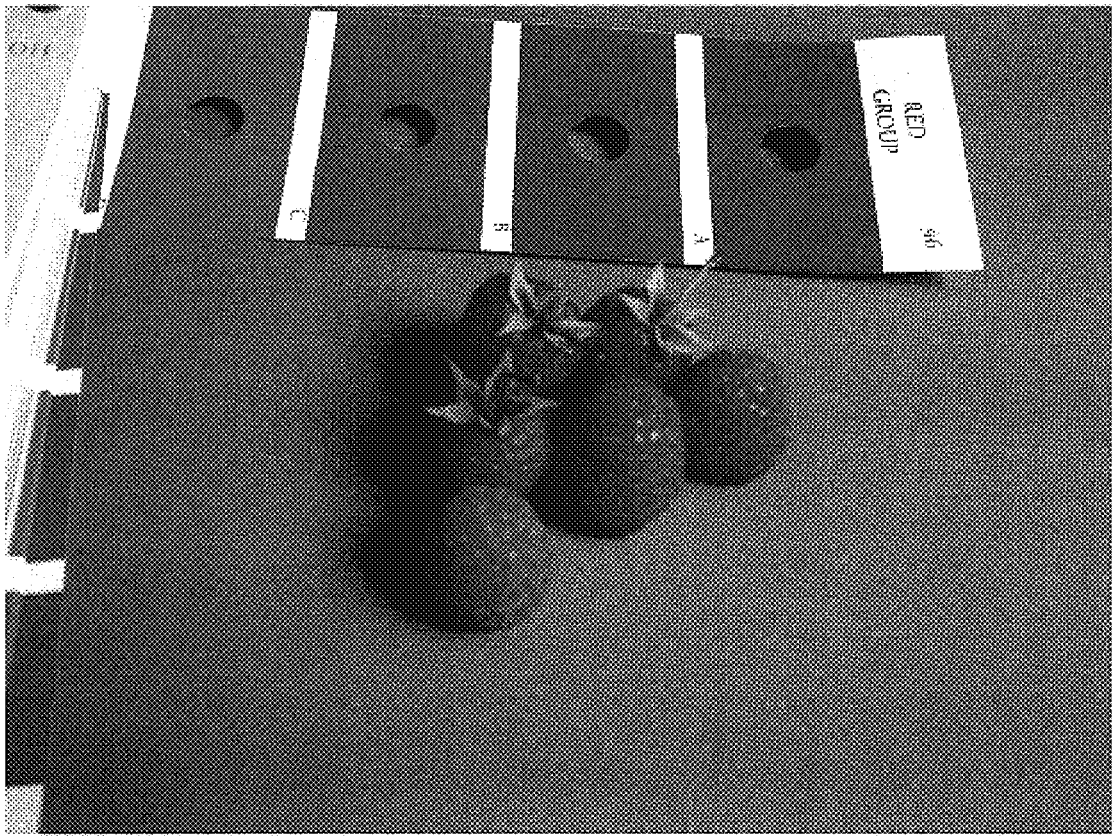
FIG. 7 shows the slight grey-pink blush of 'Georgia' sepals when the fruit is ripe and Royal Horticultural Society colour plate 46 ($2^{nd}$ growing season).
Figure 8:
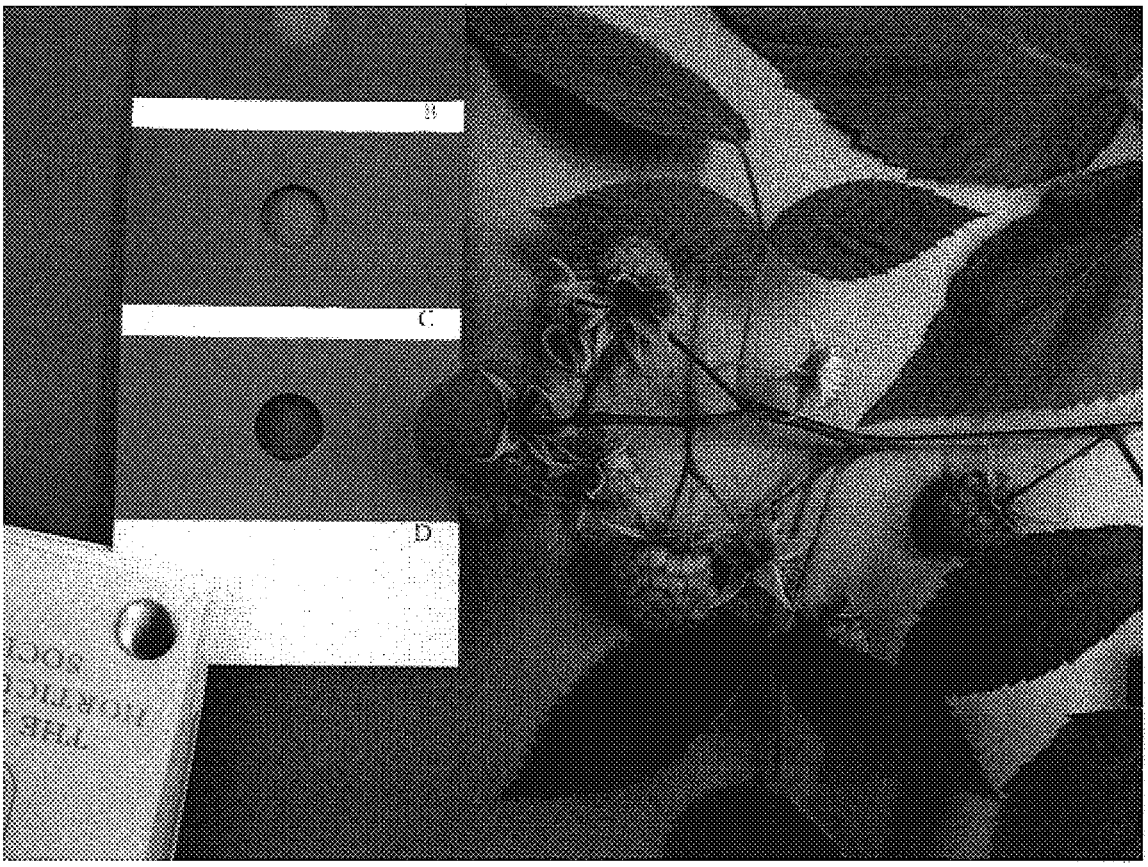
FIG. 8 shows the fruit of 'Georgia' attached to a fruiting truss removed from the apical section of a floricane and Royal Horticultural Society colour plate 46 ($2^{nd}$ growing season).

Flowers do not normally occur on primocanes. The unscented flower morphology and early fruit morphology is typical of most red raspberry cultivars, five white 0.5 cm long petals (Royal Horticultural Society colour plate No. 155D) abscise after pollination (FIG. 6). Five 0.9 cm long grey green sepals (Royal Horticultural Society colour plate No. 194B) are green until harvest but often have a slight grey pink blush (Royal Horticultural Society colour plate No. 186C) (FIG. 7). This blush is very much less common in 'Glen Ample'. 'Georgia' can have over 100 pistils on early flowers to less than 50 on later flowers and over 70 anthers; the pollen sac color resembles Royal Horticultural Society colour plate No. 158B (see FIG. 6). Except for the pink blush on the sepals, when the fruit is ripe, none of these traits can be used to identify 'Georgia'. Flower trusses are typical cymose clusters, apical trusses average 8.0 flowers per inflorescence (see FIG. 8).

Figure 9:
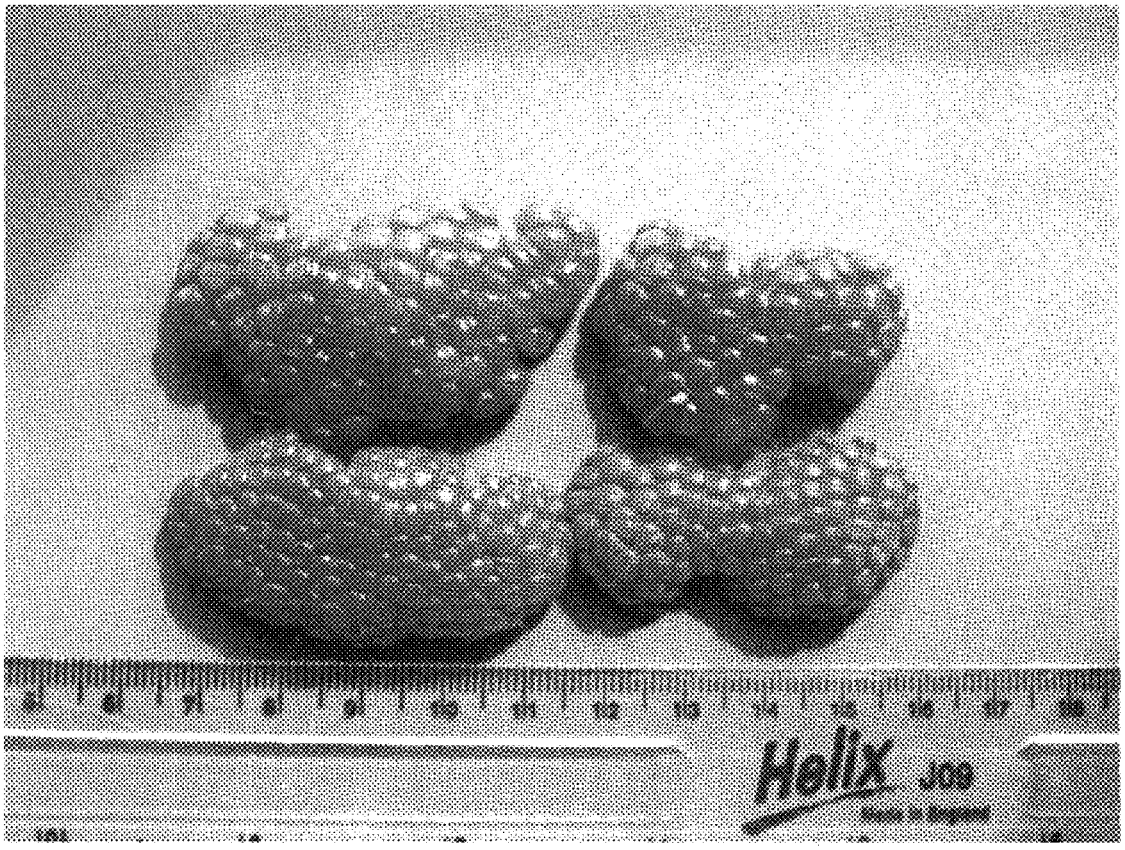
FIG. 9 shows 'Georgia' (nearest to ruler) and 'Glen Ample' fruit "peels" demonstrating the drupelet size of each cultivar and the pileated nature of 'Georgia' (row closest to ruler) and 'Glen Ample' (farthest away from ruler) drupelets ($2^{nd}$ growing season).
Figure 10:
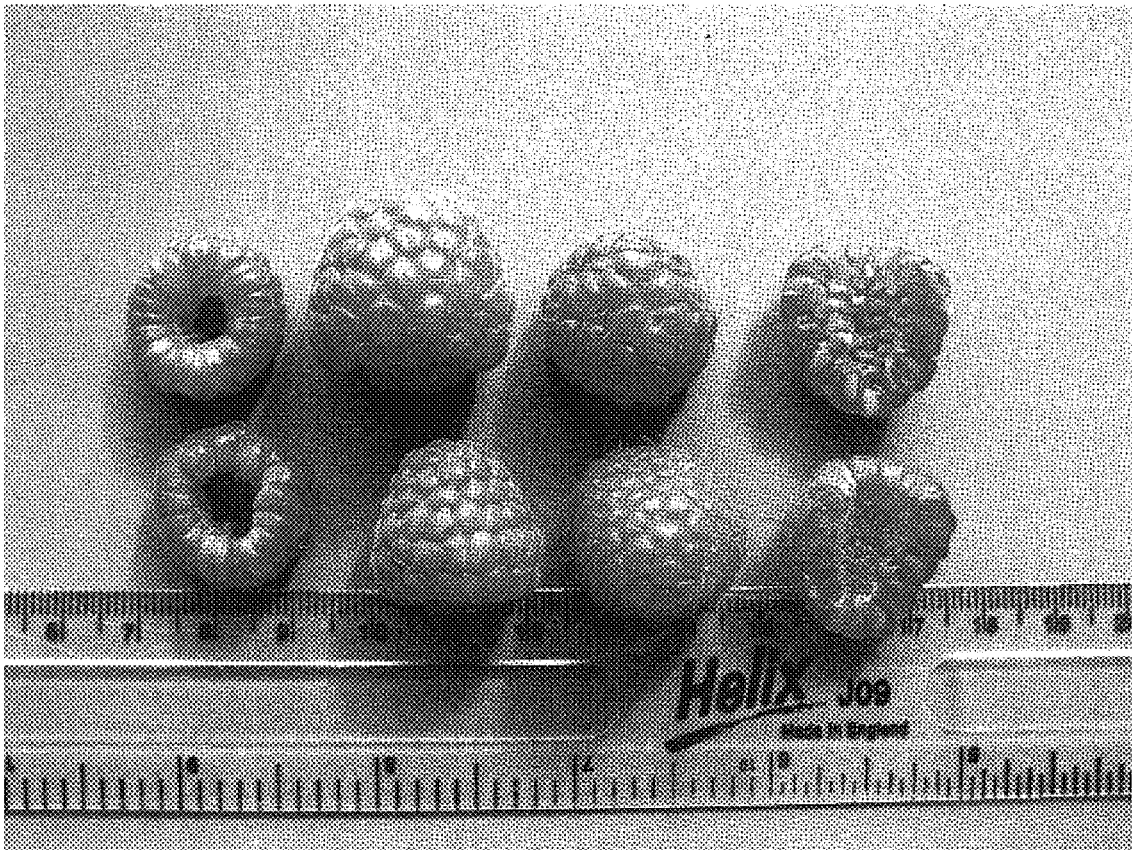
FIG. 10 shows the typical shape of 'Georgia' fruit ($2^{nd}$ growing season).

Fruit are readily distinguishable by round shape and pileation for this variety at 10 days post pollination (FIGS. 9 and 10). Fruit ripens within 30 days after pollination on floricanes in the United Kingdom. Fruit is ripe beginning early to late June in the Mid-Atlantic region. In southeastern United Kingdom, the 5%, 50% and 95% ripe dates were: May 29, June 19 and July 10. 'Georgia' fruit is highly symmetrical, has an even collar and has a slight amount of pubescence when ripe. 'Georgia' drupelets have a slight, 1 mm long, pileation basal to where the dried style is attached, resulting is a distinctive downturning of the relect stigma-style (FIG. 9). This pileation is also common for 'Glen Ample' (U.S. Plant Pat. No. 11,418). Fruit is very firm and cohesive when picked. Although color darkens to red-purple when overripe, 'Georgia' fruit firmness and cohesiveness is retained in storage. Fruit is easy to pick even when unripe and colored pink to red. In the US., 'Georgia' fruit will often tear across the drupelets rather than separate from each other. The fruit is very cohesive in both locations. Due to these traits, fruit are difficult to shatter under pressure of hand harvest, unlike 'Glen Ample', 'Lauren', 'Titan' and other spring bearing cultivars.

The fruit of 'Georgia' is very symmetrical. It is common to observe perfectly curvilinear rows of drupelets, i.e. along the latitudinal circumference of the fruit. In Faversham, Kent, United Kingdom in 2005, the midseason, 3 gram mature fruit length was 1.85 cm, while width was 1.82 cm, producing a ratio of 1:1, although earlier fruit is very slightly more elongated. Midseason fruit have 11.8 drupelets per $cm^2$, and average 3.0 grams fresh weight (FIG. 9). Midseason fruit weight for 'Glen Ample', which also has pileated drupelets, is 3.5 grams and fruit average 8 drupelets per $cm^2$ (FIG. 9). The mid-season 'Georgia' fruit has a receptacle cavity about 33% of the fruit diameter, thus the drupelets are the same width as the cavity (FIG. 10). This ratio is very similar to the typical round conic firm and cohesive fall bearing cultivar 'Josephine', which has a cavity 40% of the fruit diameter and the spring bearing cultivar 'Glen Ample', which also has a cavity 33% of the diameter of its fruit. Fruit diameter to length ratio on midseason fruit of 'Glen Ample' of 3 grams is usually very close to 1:1, this ratio also changes on larger and smaller fruit.

'Georgia' fruit are medium to dark red when ripe, closely resembling the hue of Royal Horticultural Society colour plate No. 46D (see FIG. 10). When fully or over ripe, or upon 7 days storage, fruit develops a medium intensity red color, resembling Royal Horticultural Society colour plate No. 46C. The fruit does not break down after at least one week of storage in ventilated plastic, pint-sized "clam shells" in a common household refrigerator. The temperature of the refrigerator averaged 40 F. Flavor is sweet with an average % soluble solids reading by refractory of 12.7%, compared to 11.0% for 'Glen Ampule'. The aroma is strong and characteristic of red raspberry and has been accepted by national food chains in the United Kingdom. 'Georgia' fruit is suitable for commercial shipment. 'Georgia' fruit has sufficient flavor and ease of picking to benefit a pick-your-own marketing operation.

The plant is field resistant to anthracnose and verticillium wilt. The plant is not very susceptible to late season leaf rust (yellow rust) in the mid-Atlantic states. The plant's reaction to Phyophthora fragrance root rot is probably resistant, based on field reaction, not on controlled testing. Fruit is usually free from rot in the field, more so than 'Anne' and 'Caroline', but not 'Josephine'.

FRUIT PRODUCTION

'Georgia' has been tested in a 50 plant trial in a commercial field in Faversham, Kent, England. The following data were collected in the spring and summer of 2005. Plants were planted in April 2004, the data below could be classified as first commercial plant yield. The spring of 2005 was characterized by normal se United Kingdom temperatures, but below normal rainfall. Data are averaged grams per cane for the dates reported. Yield from three dates were summed and reported below as one number.

| Date | 'Georgia' | 'Glen Ample' |
|---|---|---|
| May 25-27 | 20.2 | 0.0 |
| May 29-31 | 41.9 | 14.2 |
| June 1-3 | 27.9 | 22.4 |

-continued

| Date | 'Georgia' | 'Glen Ample' |
|---|---|---|
| June 4-7 | 28.7 | 26.3 |
| June 8-10 | 28.0 | 30.5 |
| June 11-14 | 36.5 | 39.3 |
| June 15-17 | 38.0 | 23.1 |
| June 18-20 | 34.3 | 24.0 |
| June 21-23 | 53.0 | 41.9 |
| June 24-26 | 36.4 | 35.3 |
| June 27-29 | 41.7 | 49.5 |
| June 30-July 2 | 31.4 | 28.0 |
| July 3-6 | 24.0 | 46.8 |
| July 7-10 | 13.0 | 34.8 |
| July 11-14 | 9.8 | 12.9 |
| July 15-19 | 10.0 | 0.0 |
| Total yield | 481 | 437 |

'Georgia' has been asexually reproduced by tissue culture, dormant cuttings and mist-propagated root sucker cuttings for three years at the University of Maryland and Edward Vinson Ltd in Faversham, Kent England. Suckering is moderate to high and the plant readily establishes either in tissue culture or in a mist rooting chamber. Such propagules maintain the distinctive characteristics of 'Georgia', including thornlessness of the canes, earliness to fruit and definitive fruit quality traits including pileation of the fruit and fruit sweetness and firmness. Thus, the observed plant retains its distinctive characteristics and reproduces true to type in successive generations.

What is claimed:

1. A new and distinct spring bearing red raspberry plant known as 'Georgia' as described therein, illustrated and identified by the characteristics set forth above.

* * * * *